United States Patent
Forohar et al.

(10) Patent No.: US 6,232,479 B1
(45) Date of Patent: May 15, 2001

(54) SUBSTITUTED CYCLOTETRAPHOPHAZENE COMPOUND AND METHOD OF PRODUCING THE SAME

(75) Inventors: Farhad Forohar, Flanders; Paritosh R. Dave, Bridgewater; Sury Iyer, Randolph, all of NJ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/639,268

(22) Filed: Aug. 15, 2000

(51) Int. Cl.$^7$ .............. C07F 9/02; C06B 49/00; C06B 43/00
(52) U.S. Cl. .............. 552/3; 568/12; 149/108.6; 149/121
(58) Field of Search .............. 149/108.6, 121; 552/3; 568/12

(56) References Cited

PUBLICATIONS

Database CAPLUS on STN, Acc. No. 1981:408685, Heitsch et al., 'Fire retardant textiles—cotton treated with amidophosphazene.' Org. Coat. Plast. Chem. (1979), 41, pp. 97–102 (abstract).*

* cited by examiner

Primary Examiner—Johann Richter
Assistant Examiner—Brian J. Davis
(74) Attorney, Agent, or Firm—Robert Beam; John F. Moran; Michael C. Sachs

(57) ABSTRACT

A novel cyclotetraphosphzene compound, 1,1-diamino-3, 3,5,5,7,7-hexaazidocyclotetraphosphazene, is disclosed which has application as an energetic compound and percussion primer. Also disclosed is a method of preparing the compound.

4 Claims, 5 Drawing Sheets

SUBSTITUTED CYCLOTETRAPHOPHAZENE COMPOUND AND METHOD OF PRODUCING THE SAME

STATEMENT REGARDING FEDERALLY SPONSORED RESEARCH OR DEVELOPMENT

The invention described herein may be made, used, or licensed by or for the United States Government for Governmental purposes without the payment of any royalties thereon or therefor.

CROSS REFERENCE TO RELATED APPLICATIONS

None

BACKGROUND OF THE INVENTION

1. Field of the Invention

The present invention relates to a novel cyclotetraphosphazene compound and a method of producing the same. In particular, the present invention relates to 1,1-diamino-3,3,5,5,7,7-hexaazidocyclotetraphosphazene, which has shown to be useful as an energetic composition and a percussion primer.

2. Description of Related Art

Many energetic compositions, and particularly percussion primers, are environmentally objectionable. Prior art percussion primers typically use lead azide, lead styphnate, antimony sulfide, barium nitrate, mercury fulminate and other materials containing heavy metals that are known to contribute to environmental pollution during manufacturing and use. Firing of small arms, especially in indoor firing ranges, releases clouds of hazardous gases in addition to increased contamination of the soil and ground water.

The need for an alternative primary explosive that is more environmentally friendly has been felt for some time, and several attempts have been made to provide such a compound.

U.S. Pat. No. 5,717,159 issued to Dixon, Martin, and Thompson on Feb. 10, 1998. This reference is entitled Lead-Free Percussion Primer Mixes Based on Metastable Interstitial Composite (MIC) Technology, and discloses a mixture of aluminum powder having an outer coating of aluminum oxide and either molybdenum trioxide or polytetrafluoroethylene.

U.S. Pat. No. 5,993,577 issued to Erickson, Melberg and Sandstrom on Nov. 30, 1999. This reference is entitled Lead-Free, Heavy-Metal-Free Rim-Fire Priming Composition, and discloses a combination of diazodinitrophenol, tetracene, ground glass, and a lead-free, heavy-metal-free oxidizer, together with a binder and a dye.

Cyclotriphosphazenes have been reported as energetic compounds in *Novel Spiro Substituted Cyclotriphosphazenes Incorporating Ethylenedinitramine Units,* Dave, et al., Phosphorus, Sulfur, and Silicon, 1994, vol. 90, pp. 175–184, and in *Synthesis Of Ethylenedinitramine Deriatives Of Fluorocyclotriphosphazenes,* Forohar, et al., Phosphorus, Sulfur, and Silicon, 1995, vol. 101, pp. 161–166.

BRIEF SUMMARY OF THE INVENTION

OBJECTS OF THE INVENTION

It is an object of the present invention to provide an environmentally friendly energetic compound.

It is a further object of the present invention to provide an environmentally friendly percussion primer.

It is a still further object of the present invention to provide an environmentally friendly energetic compound useful as a percussion primer that meets or exceeds the properties of the prior art.

The other objects, features and advantages of the present invention will become more apparent in light of the following detailed description of the preferred embodiment thereof.

SUMMARY OF THE INVENTION

According to the present invention, a novel compound, 1,1-diamino-3,3,5,5,7,7-hexaazidocyclotetraphosphazene, is disclosed.

According to another embodiment of the present invention, there is disclosed a novel energetic composition comprising 1,1-diamino-3,3,5,5,7,7-hexaazidocyclotetraphosphazene.

According to a further embodiment of the present invention, there is disclosed a novel percussion primer comprising 1,1-diamino-3,3,5,5,7,7-hexaazidocyclotetraphosphazene.

According to a still further embodiment of the present invention, there is disclosed a method of preparation of 1,1-diamino-3,3,5,5,7,7-hexaazidocyclotetraphosphazene, which method comprises the steps of:

a. reacting a quantity of octachlorocyclotetraphosphazene with ammonium hydroxide in ether to produce isomers of diaminohexachlorocyclotetraphosphazene;

b. isolating 1,1-diamino-3,3,5,5,7,7-hexachlorocyclotetraphosphazene from the reaction product of step (a);

c. reacting the 1,1-diamino-3,3,5,5,7,7-hexachlorocyclotetraphosphazene with sodium azide in acetone to produce 1,1-diamino-3,3,5,5,7,7-hexaazidocyclotetraphosphazene.

DETAILED DESCRIPTION OF THE INVENTION

Phosphazenes are phosphorous-nitrogen ring compounds which have two substituents attached to each phosphorous atom. These substituents can be manipulated to place a variety of different groups on the ring system. Two major types of phosphazenes appear to have commercial use. The first class includes six membered ring cyclotriphosphazenes such as hexachlorocyclotriphosphazene. The second class includes eight membered ring cyclotetraphosphazenes such as octachlorocyclotetraphosphazene.

The present invention comprises a novel cyclotetraphosphazene derived from octachlorocyclotetraphosphazene, which is commercially available from Phosphazene Custom Synthesis, Inc., 2820 East College Avenue, Suite N, State College, Pa. 16801. The novel compound of the present invention, 1,1-diamino-3,3,5,5,7,7-hexaazidocyclotetraphosphazene, was synthesized and identified as a new class of environmentally friendly primer explosive. It has demonstrated positive experimental results for application in small arms ammunition.

This novel compound of the present invention, 1,1-diamino-3,3,5,5,7,7-hexaazidocyclotetraphosphazene, was synthesized from octachlorocyclotetraphosphazene in the following manner. First, a quantity of octachlorocyclotetraphosphazene was reacted with ammonium hydroxide in ether to produce isomers of diaminohexachlorocyclotetraphosphazene. This reaction has been reported in the literature. See, J. K. Fincham, R. A. Shaw, "Phosphorous-Nitrogen Compounds. Part 62". *Phosphorous, Sulfur, and Silicon,* 1990, Vol. 47, p. 109. Then, after isolating 1,1-diamino-3,3,5,5,7,7-hexachlorocyclotetraphosphazene from the reaction products of the first step, the 1,1-diamino-3,3,5,5,7,7-hexachlorocyclotetraphosphazene was reacted with sodium azide in acetone to produce 1,1-diamino-3,3,5,5,7,7-hexaazidocyclotetraphosphazene, which was then crystallized from solution.

Figure 1:
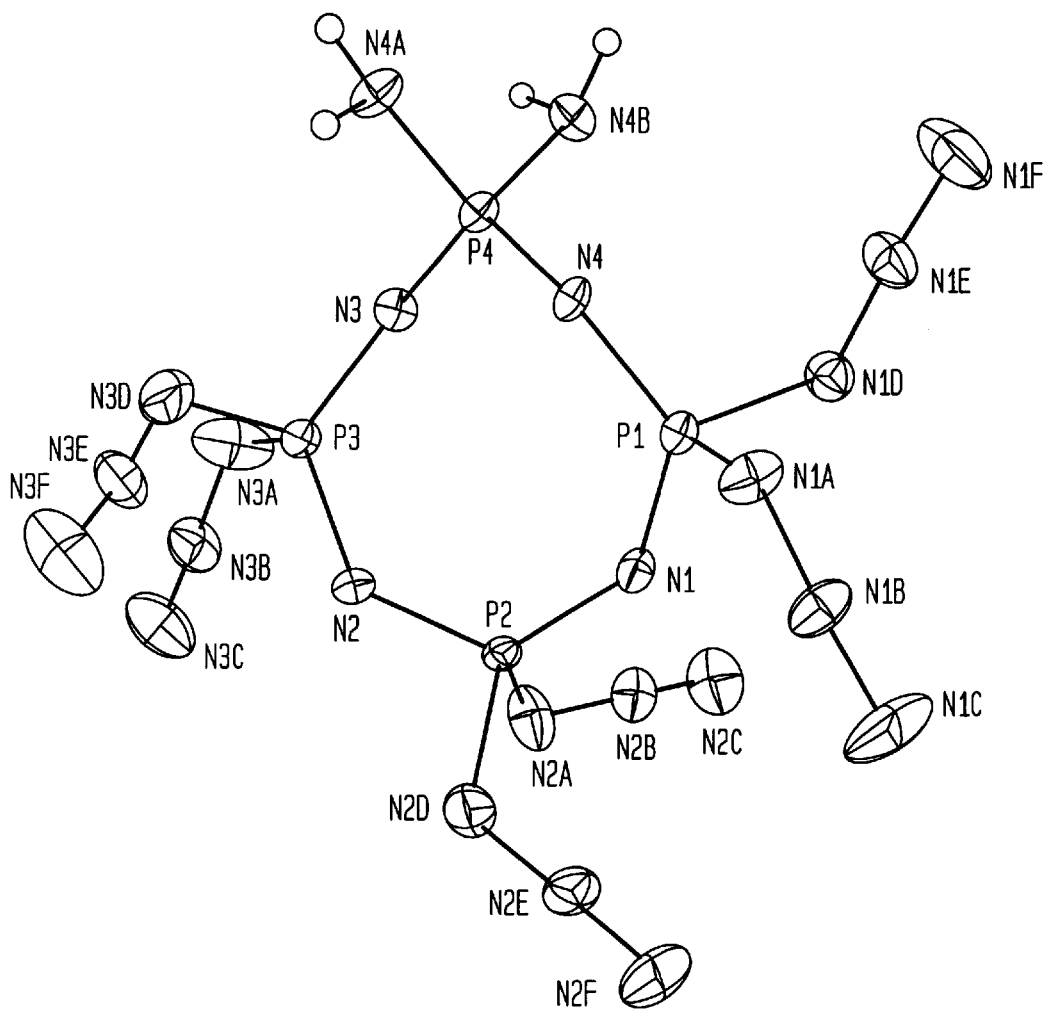
FIG. 1 shows the structure of 1,1-diamino-3,3,5,5,7,7-hexaazidocyclotetraphosphazene as determined X-ray crystallography.
Figure 2:
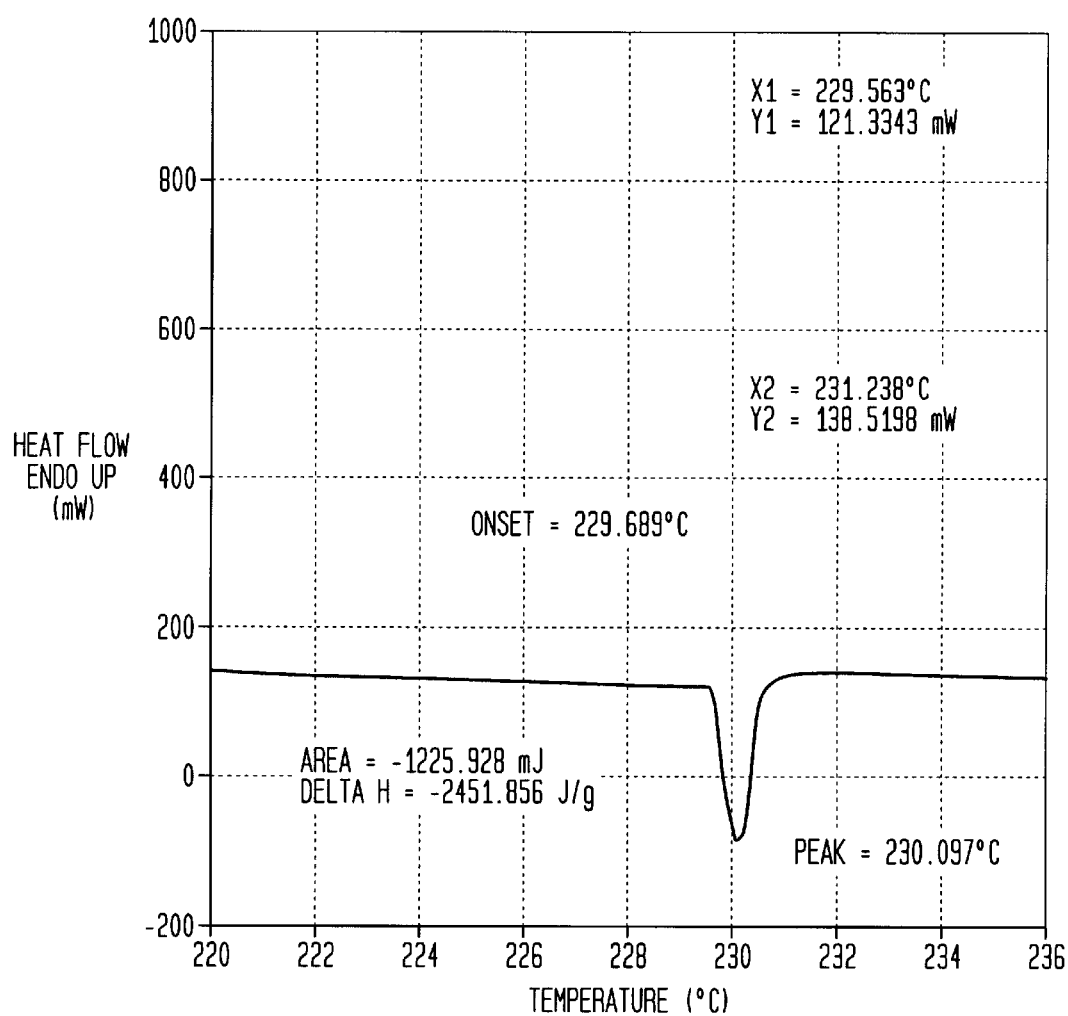
FIG. 2 shows the results of Differential Scanning Calorimetry (DSC) of 1,1-diamino-3,3,5,5,7,7-hexaazidocyclotetraphosphazene.
Figure 3:
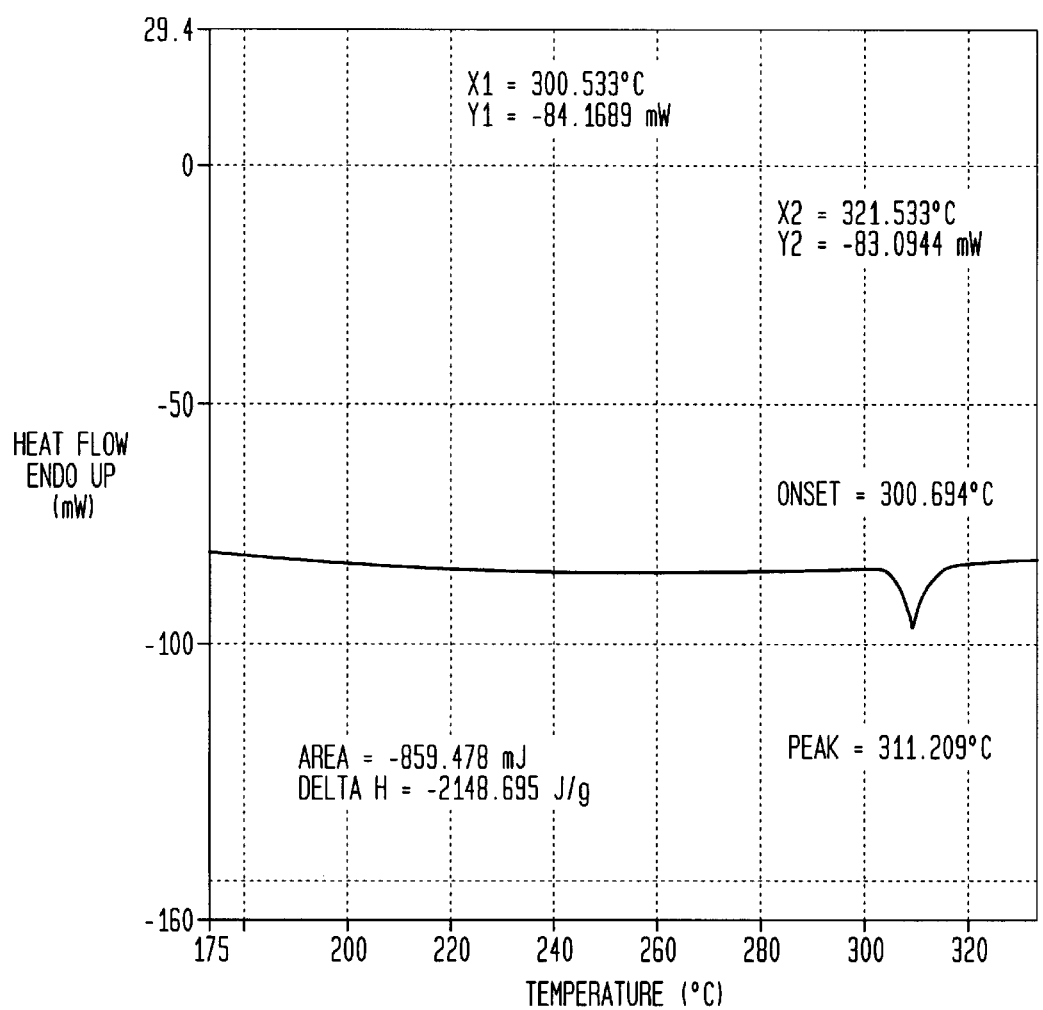
FIG. 3 shows the results of Differential Scanning Calorimetry (DSC) of lead azide.

A white crystalline material, the chemical structure of the compound of the present invention, 1,1-diamino-3,3,5,5,7,7-hexaazidocyclotetraphosphazene, was confirmed by X-ray crystallography, as shown in FIG. 1, and melts at 72–74° Celcius. Differential Scanning Calorimetry (DSC) indicated that the novel compound decomposes violently at 230° Celcius, as shown in FIG. 2. The Differential Scanning Calorimetry also showed a Delta H of –2451 Joules per gram for the novel compound, which compares favorably to the Delta H value of –2148 Joules per gram for lead azide, measured on the same instrument, as shown in FIG. 3. This indicates a release of approximately fifteen percent (15%) more energy for the novel compound of the present invention.

EXAMPLE 1

Synthesis of 1,1-diamino-3,3,5,5,7,7-hexachlorocyclotetraphosphazene

A two-liter four-neck round-bottom flask was equipped with a condenser, an addition funnel, a mechanical stirrer, and a stopcock. One hundred and fifty grams (150 g.) of sodium sulfate, five hundred milliliters (500 ml) of ethyl ether, and eleven and two-tenths grams (11.2 g.) of octachlorocyclotetraphosphazene were added to the round bottom flask. An ice bath was placed under the flask and the mixture was stirred vigorously by the mechanical stirrer. Seven milliliters (7 ml) of reagent grade (17M) ammonium hydroxide in a further one hundred milliliters (100 ml) of ethyl ether was transferred into the flask by way of the addition funnel, and slowly added to the reaction mixture over a two hour (2 hour) period. After the addition was completed, the mixture was stirred at ice bath temperature for an additional one-half hour (½ hour).

The reaction mixture was then filtered to remove the sodium sulfate and the ammonium chloride by-product. The resulting clear solution obtained after filtration was subjected to a rotary evaporator to remove the solvent. A white solid crude product was obtained after solvent removal, and the solvent could, in principle, be recycled.

The white solid was ground and crushed to a finer particle size and stirred in three hundred milliliters (300 ml) of petroleum ether, then recovered by filtration. About four hundred milliliters of cyclohexane was added to the solid and the resulting suspension was refluxed for thirty minutes (30 min.) and quickly filtered. Three and six-tenths grams (3.6 g.) of a white solid was collected. Based upon the measured melting point of two hundred and five to two hundred and seven degrees Celsius (205–207° C.), it is believed that this was an isomer, 1,5-diamino-1,3,3,5,7,7-hexachlorocyclotetraphosphazene. An additional one and three-tenths grams (1.3 g.) of solid product containing the desired product along with some impurities was obtained from the petroleum ether solution after concentration.

The clear cyclohexane solution was then concentrated by rotary evaporation to remove the solvent and four and nine-tenths grams (4.9 g.) of 1,1-diamino-3,3,5,5,7,7-hexachlorocyclotetraphosphazene was obtained as a white solid which had a melting point of eighty-four to eighty-six degrees Celsius (84–86° C.). This represented eleven and five-tenths milliMoles (11.5 mmol) and a yield of forty-eight percent (48%).

EXAMPLE 2

Synthesis of 1,1-diamino-3,3,5,5,7,7-hexaazidocyclotetraphosphazene

Three and two-tenths grams (3.2 g.) of 1,1-diamino-3,3,5,5,7,7,-hexachlorocyclotetraphosphazene, six grams (6.0 g.) of sodium azide, and one hundred and fifty milliliters (150 ml) of acetone were placed into a five hundred milliliter (500 ml) round bottom flask containing a stirring bar. The resulting suspension was stirred at room temperature for twenty-four hours (24 hours). The suspension was then filtered to remove the excess sodium azide and the sodium chloride by-product.

The resulting clear solution was then very carefully concentrated by rotary evaporation to obtain an oil. After a short time, the oil was crystallized by itself into a paste. A small quantity, approximately three milliliters (~3 ml.) of cold 95% ethanol was added to this to separate and collect two and two-tenths grams (2.2 g.) of crystals by filtration. A melting point of seventy-two to seventy-four degrees Celsius (72–74° C.) confirmed that the product was 1,1-diamino-3,3,5,5,7,7-hexaazidocyclotetraphosphazene, which was further confirmed by Phosphorous Nuclear Magnetic Resonance ($^{31}$P NMR). This represented four and seven-tenths milliMoles (4.7 mmol) and a yield of sixty-three percent (63%). Some product remained in solution in the ethanol and could, in principle, be recovered by re-crystallization.

EXAMPLE 3

Figure 4:
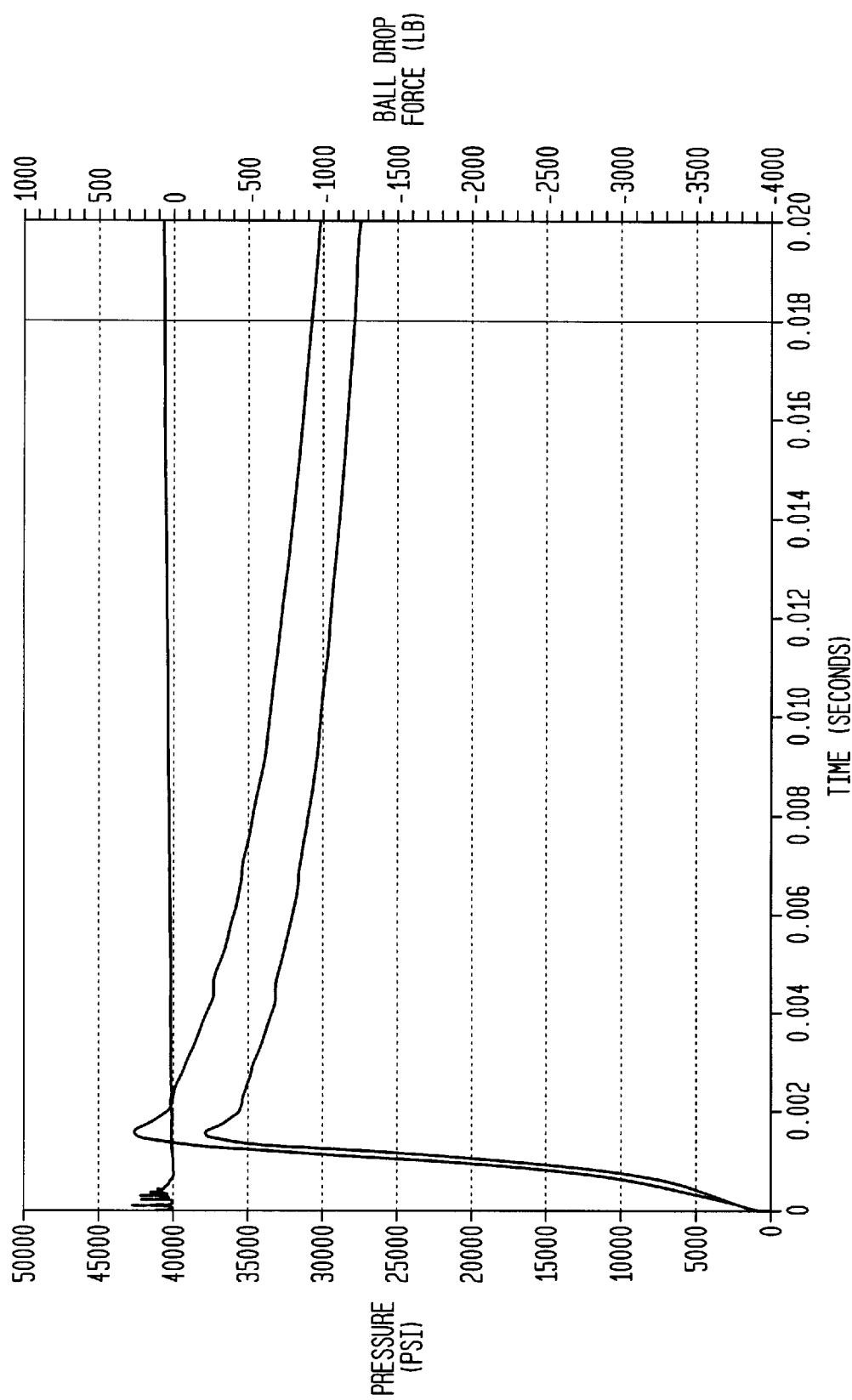
FIG. 4 shows the results of a Primer Ignitability Test of 1,1-diamino-3,3,5,5,7,7-hexaazidocyclotetraphosphazene.

In a commercial #41 primer, the standard FA-956 primer mixture was replaced with the novel compound 1,1-diamino-3,3,5,5,7,7-hexaazidocyclotetraphosphazene of the present invention. The resulting Primer Ignitability test, FIG. 4, shows the successful detonation of the propellant by the novel compound of the present invention. Further, a comparison of the results of a Primer Ignitability test of the standard FA-956 mixture, containing lead styphnate, barium nitrate, pentaerythrol tetranitrate, antimony sulfide, tetracene, and aluminum, shown in FIG. 5, reveals that the novel compound of the present invention recorded a faster detonation time and a more efficient ignition.

Figure 5:
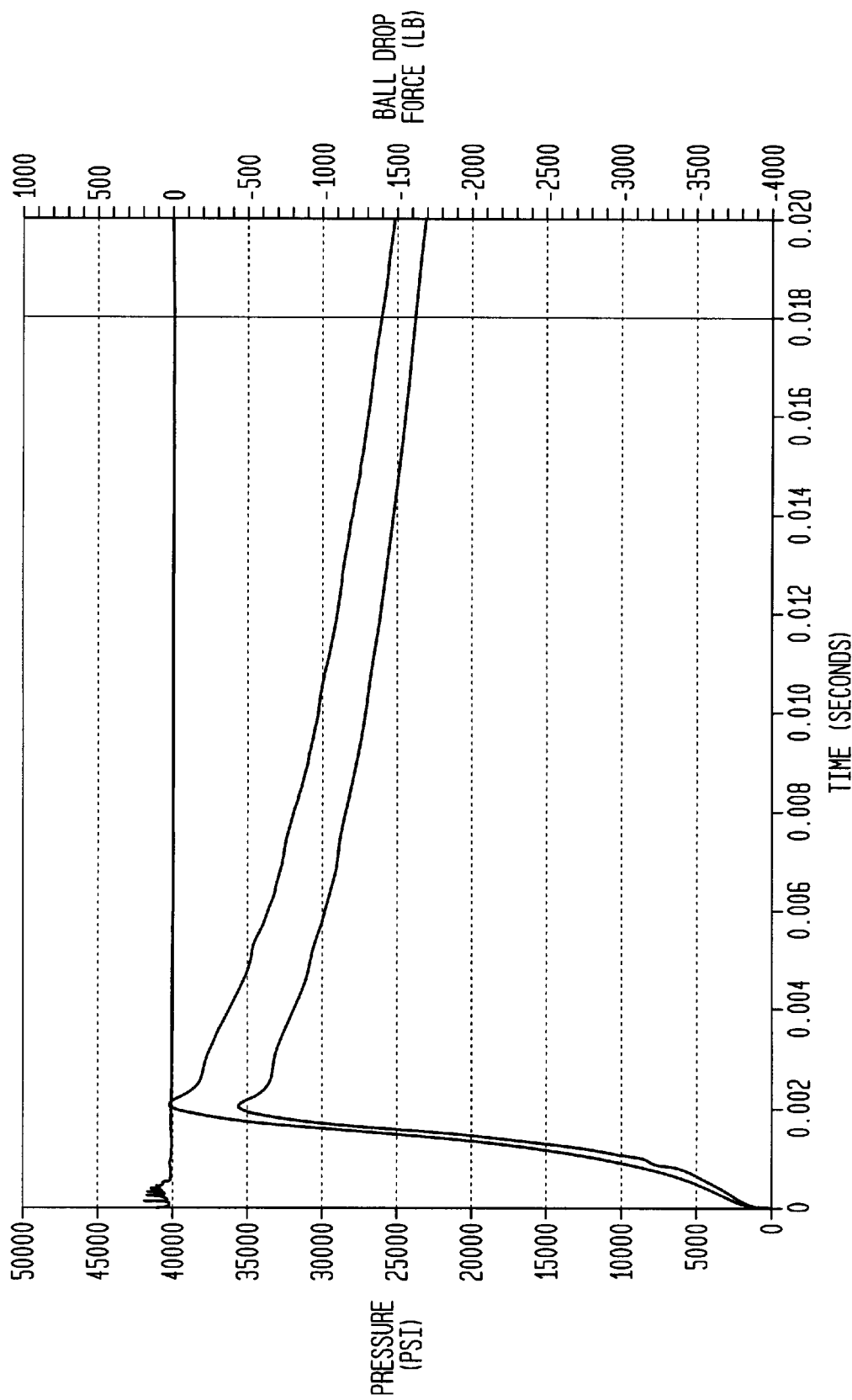
FIG. 5 shows the results of a Primer Ignitability Test of a standard FA-956 primer mixture.

As seen in FIG. 5, the standard primer mixture detonated at two milliseconds (0.002 sec.) and generated a maximum pressure of forty thousand pounds per square inch (40,000 psi). The novel compound of the present invention, however, as seen in FIG. 4, detonated earlier, at approximately one and a half milliseconds (0.0015 sec.) and generated a greater amount of pressure, a maximum pressure of about forty-three thousand pounds per square inch (43,000 psi).

A comparison of the molecular formula of lead azide, $Pb(N_3)_2$, and the novel compound of the present invention $(P_4N_4)(N_3)_6(NH_2)_2$, indicates that the novel compound of the present invention contain a greater number of energetic moieties than lead azide. Lead azide has only six nitrogen atoms per molecule while the novel compound of the present invention has 24 nitrogen atoms. Assuming total conversion of nitrogen atoms to nitrogen gas, the novel compound of the present invention can generate 3.6 times more nitrogen gas than lead azide. In terms of the mass balance of each molecule, lead azide contains seventy-one percent (71%) of the non-energetic heavy-metal lead and only twenty-one percent (21%) nitrogen. The novel compound of the present invention, by comparison, contains seventy-two percent (72%) nitrogen, twenty-seven percent (27%) phosphorous, and one percent (1%) hydrogen. This comparison indicates that the expandable gases generated by the decomposition of the novel compound of the present invention are superior to those generated by lead azide.

Other features, advantages, and specific embodiments of this information will become readily apparent to those exercising ordinary skill in the art after reading the foregoing disclosures. These specific embodiments are within the scope of the claimed subject matter unless otherwise expressly indicated to the contrary. Moreover, while specific embodiments of this invention have been described in considerable detail, variations and modifications of these embodiments can be effected without departing from the spirit and scope of this invention as disclosed and claimed.

What is claimed is:

1. 1,1-diamino-3,3,5,5,7,7-hexaazidocyclotetraphosphazene.

2. A percussion primer comprising 1,1-diamino-3,3,5,5,7,7-hexaazidocyclotetraphosphazene.

3. An energetic composition comprising 1,1-diamino-3,3,5,5,7,7-hexaazidocyclotetraphosphazene.

4. A method of preparation of 1,1-diamino-3,3,5,5,7,7-hexaazidocyclotetraphosphazene, which method comprises the steps of:

a. reacting a quantity of octachlorocyclotetraphosphazene with ammonium hydroxide in ether to produce isomers of diaminohexachlorocyclotetraphosphazene;

b. isolating 1,1-diamino-3,3,5,5,7,7-hexachlorocyclotetraphosphazene from the reaction product of step (a);

c. reacting the 1,1-diamino-3,3,5,5,7,7-hexachlorocyclotetraphosphazene with sodium azide in acetone to produce 1,1-diamino-3,3,5,5,7,7-hexaazidocyclotetraphosphazene.

* * * * *